(12) United States Patent
Mewshaw et al.

(10) Patent No.: US 6,200,994 B1
(45) Date of Patent: Mar. 13, 2001

(54) 1,4-DISUBSTITUTED CYCLOHEXANE DERIVATIVES FOR THE TREATMENT OF DEPRESSION

(75) Inventors: Richard E. Mewshaw, King of Prussia; Reinhardt B. Baudy, Doylestown, both of PA (US)

(73) Assignee: American Home Products Corp, Madison, NJ (US)

( * ) Notice: Subject to any disclaimer, the term of this patent is extended or adjusted under 35 U.S.C. 154(b) by 0 days.

(21) Appl. No.: 09/475,384

(22) Filed: Dec. 30, 1999

Related U.S. Application Data
(60) Provisional application No. 06/135,116, filed on Jan. 7, 1999.

(51) Int. Cl.[7] .................. C07D 401/08; A61K 31/4418
(52) U.S. Cl. .................. 514/339; 514/323; 514/255; 546/277.4; 546/201; 544/373
(58) Field of Search .................. 514/339, 326, 514/255; 546/277.4, 201; 544/373

(56) References Cited

U.S. PATENT DOCUMENTS

| | | | |
|---|---|---|---|
| 5,322,851 | 6/1994 | Perregaard et al. | 546/193 |
| 5,468,767 | 11/1995 | Cipollina et al. | 514/414 |
| 5,622,951 | 4/1997 | Ward et al. | 514/253 |

FOREIGN PATENT DOCUMENTS

| | | |
|---|---|---|
| 0387603 | 2/1990 | (EP). |
| 0431579 | 12/1990 | (EP). |
| 0465398 | 6/1991 | (EP). |
| 0733628 | 3/1996 | (EP). |
| 0908458 | 9/1998 | (EP). |
| WO9212977 | 8/1992 | (WO). |
| WO 9310092 | 5/1993 | (WO). |
| WO9415928 | 7/1994 | (WO). |

OTHER PUBLICATIONS

Le Poul et al., *Arch. Pharmacol*, 352:141 (1995).
Artigas et al., *Trends Neurosci.*, 19:378–383 (1996).

*Primary Examiner*—Jane Fan
(74) *Attorney, Agent, or Firm*—Joseph M. Mazzarese

(57) ABSTRACT

Compounds useful for the treatment of disorders of the serotonin-affected neurological systems are provided which have the following formula:

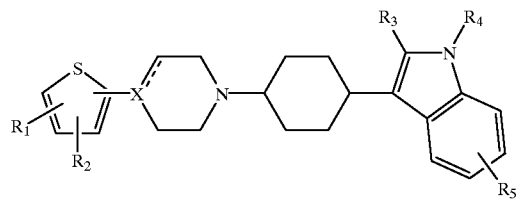

wherein:
X is carbon or nitrogen;
$R_1$ and $R_2$ are each, independently, hydrogen, halogen, $CF_3$, alkyl, alkoxy, or $MeSO2_4$;
$R_3$ is hydrogen, halogen, or alkyl;
$R_4$ is hydrogen, alkyl, alkylaryl, or aryl; and
$R_5$ is hydrogen, halogen, $CF_3$, CN, carbamide, or alkoxy; or
pharmaceutically acceptable salts thereof.

6 Claims, No Drawings

1,4-DISUBSTITUTED CYCLOHEXANE DERIVATIVES FOR THE TREATMENT OF DEPRESSION

CROSS REFERENCE TO RELATED APPLICATIONS

This application claims the benefit of U.S. Provisional Application No. 60/135,116, which was converted from U.S. patent application Ser. No. 09/226,552 filed Jan. 7, 1999.

FIELD OF INVENTION

This invention relates to compounds useful for the treatment of diseases affected by disorders of the serotonin-affected neurological systems, such as depression and anxiety. More specifically, the present invention is directed to 1,4-disubstituted cyclohexane derivatives for the treatment of such disorders.

BACKGROUND OF INVENTION

Pharmaceuticals which enhance the neurotransmission of serotonin (5-HT) are useful for the treatment of many psychiatric disorders, including depression and anxiety. The first generation of non-selective serotonin-affecting drugs operated through a variety of physiological means which caused them to possess numerous undesired side-effects. The more recently prescribed drugs, the selective serotonin reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism cannot fully account for their therapeutic activity. It is speculated that this two week induction which occurs before a full antidepressant effect is observed, is due to the involvement of the 5-HT1A autoreceptors which suppress the firing activity of 5-HT neurons, causing a dampening of the therapeutic effect. Studies suggest that after several weeks of SSRI administration, a desensitization of the 5-HT autoreceptors occurs allowing a full antidepressant effect in most patients. (See, e.g., Le Poul et al., *Arch. Pharmacol.*, 352:141 (1995)). Hence, it is believed that overriding this negative feedback by using 5HT1A antagonists would potentially increase and accelerate the clinical antidepressant response. Recent studies by Artigas et al., *Trends Neurosci.*, 19:378–383 (1996), suggest a combination of 5-HT1A activity and inhibition of 5-HT uptake within a single molecular entity can achieve a more robust and fast-acting antidepressant effect.

The present invention relates to a new class of molecules which have the ability to act at the 5-HT1A autoreceptors and concomitantly with the 5-HT transporter. Such compounds are therefore potentially useful for the treatment of depression as well as other serotonin disorders.

U.S. Pat. No. 5,468,767 reports a series of substituted indoles of the following formula for the treatment of disorders associated with dysfunction in serotonergic neurotransmission, including depression

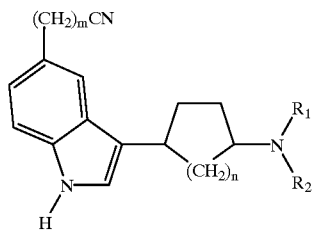

wherein $R_1$ is hydrogen or $C_{1-4}$ alkyl;
$R_2$ is $C_{1-4}$ alkyl or $(CH_2)_p Ar$;
m is zero or 1;
n is an integer from 1 to 3; and
p is zero or an integer from 1 to 4.

U.S. Pat. No. 5,622,951 discloses a series of piperazine derivatives of the following formula for the treatment of CNS disorders, including depression

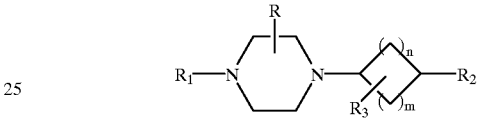

wherein R is hydrogen or one or two lower alkyl groups;
$R_1$ and $R_2$ are each the same or different mono- or bicyclic aryl or heteroaryl radicals;
$R_3$ is hydrogen, one or two of the same or different lower alkyl groups or a spirocycloalkyl group; and
n is 1 or 2 and m is 1 to 3 and the total of n+m is 2, 3 or 4.

PCT Publication No. WO 93/10092 discloses a series substituted 1,3-cycloalkenes and cycloalkanes useful in the treatment of dopaminergic disorders.

SUMMARY OF INVENTION

The compounds of this invention are arylpiperazinyl-cyclohexyl indole derivatives represented by Formula I:

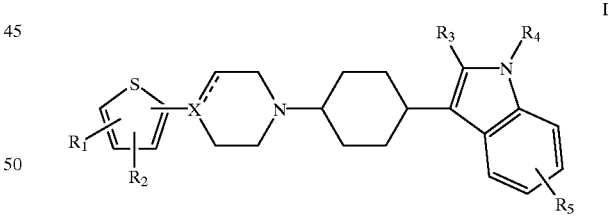

X is carbon or nitrogen;
$R_1$ and $R_2$ are each, independently, hydrogen, halogen, $CF_3$, alkyl, alkoxy, or $MeSO_2$;
$R_3$ is hydrogen, halogen, or alkyl;
$R_4$ is hydrogen, alkyl, alkylaryl, or aryl; and
$R_5$ is hydrogen, halogen, $CF_3$, CN, carbamide, or alkoxy; or
pharmaceutically acceptable salts thereof.

DETAILED DESCRIPTION OF THE INVENTION

Preferably, the compounds of the present invention are those of Formula I, wherein:

X is carbon;

$R_1$ and $R_2$ are each, independently, hydrogen or alkoxy;

$R_3$ is hydrogen;

$R_4$ is hydrogen; and $R_5$ is halogen; or pharmaceutically acceptable salts thereof.

More preferably, the compounds of the present invention are selected from:

5-Fluoro-3-{(1,4-cis)-4-[4-(3-methoxy-thiophen-2-yl)-3,6-dihydro-2H-pyridin-1-yl]-cyclohexyl}-1H-indole; and 5-Fluoro-3-{(1,4-trans)-4-[4-(3-methoxy-thiophen-2-yl)-3,6-dihydro-2H-pyridin-1-yl]cyclohexyl}-1H-indole.

As used herein, the terms "alkyl" and "alkoxy" are meant to include both straight and branched carbon chains containing 1–6 carbon atoms. The term "aryl" is meant to include aromatic radicals of 6–12 carbon atoms. The term "halogen" is meant to include fluorine, chlorine, bromine and iodine.

The compounds of this Formula I also may be used in the form of a pharmaceutically acceptable acid addition salt having the utility of the free base. Such salts, prepared by methods well known to the art, are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, benzene-sulfonic, hydrochloric, hydrobromic, sulfuric, cyclohexylsulfamic, phosphoric and nitric acids.

The compounds of the present invention may be prepared by any suitable method which will be recognized by those skilled in the art. However, the present compounds may be advantageously prepared according to Scheme 1 set forth below.

Scheme 1

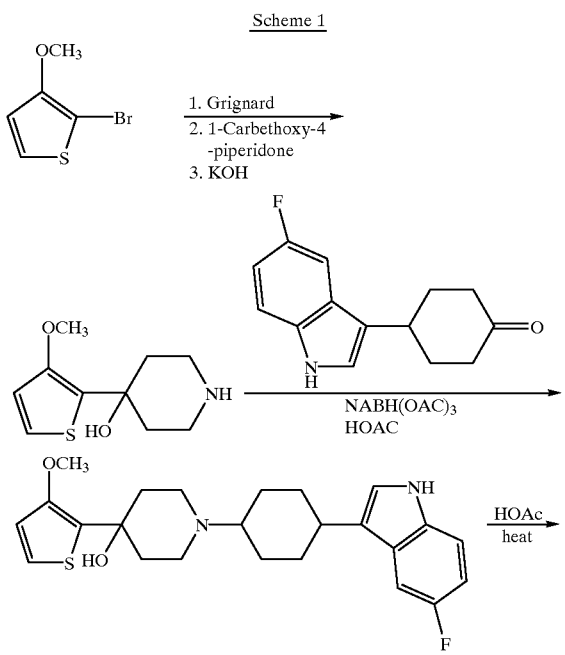

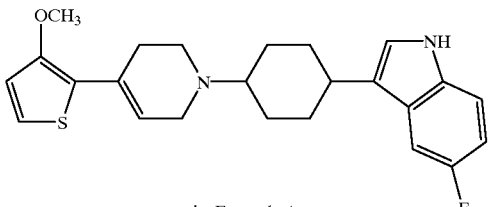

cis: Example 1
trans: Example 2

Specific exemplification of the production of representative compounds of this invention is given in the following procedures.

INTERMEDIATE 1

4-(5-Fluoro-1H-3-indolyl)-cyclohex-3-en-ethylene ketal

5-Fluoroindole (4.96 g, 0.036 mol), 1,4-cyclohexanedione monoethylene ketal (7.17 g, 0.046 mol) and potassium hydroxide (6 g, 0.043 mol) were heated to reflux in 70 ml of methanol for 6 hours. The reaction was cooled and the product was isolated by filtration and washed with water to give 8.59 g (86%) of product as a white solid: mp 153–155° C.

INTERMEDIATE 2

4-(5-Fluoro-1H-3-indolyl)-cyclohexanone ethylene ketal

A mixture of 4-(5-fluoro-1H-3-indolyl)-cyclohex-3-en-ethylene ketal (8.5 g) and 10% palladium on carbon (2.72 g) in ethanol (200 ml) was hydrogenated for 5 hours. The catalyst was filtered off and the solvent removed under vacuum. Chromatography (methanol-methylene chloride) afforded 7.55 g (82%) of product as a white solid: mp 183–185° C.

INTERMEDIATE 3

4-(5-Fluoro-1H-3-indolyl)-cyclohexanone

A solution of 4-(5-fluoro-1H-3-indolyl)-cyclohexanone ethylene ketal (2.8 g, 10 mmol) in 2 L (1:1) tetrahydrofuran-hydrochloric acid (1N) was allowed to stir at room temperature for 16 hours. The solvent was evaporated under vacuum. The crude product was dissolved in ethyl acetate, and washed with 1N sodium hydroxide (3×150 ml). The organic layer was dried over anhydrous sodium sulfate and filtered. Chromatography (40% ethyl acetate-hexanes) afforded 2.1 g (91%) of product as yellow solid: mp 112–114° C.

INTERMEDIATE 4

5-Fluoro-3-{(1,4-cis)-4-[4-(3-methoxy-thiophen-2-yl)-3,6-dihydro-2H-pyridin-1-yl]-cyclohexyl}-1H-indole A solution of 4-(5-fluoro-1H-3-indolyl)-cyclohexanone (1.32 g, 5.7 mmol), 4-hydroxy-4-(3-methoxy-thiophen-2-yl)-piperidine, produced according to the procedures set forth in U.S. Pat. No. 5,525,600 (0.5 g, 2.5 mmol), sodium triacetoxyborohydride (1.82 g, 8.6 mmol) and acetic acid (0.65 ml, 11 mmol) in 1,2-dichloroethane (20 ml) was allowed to stir at room temperature overnight. The reaction was quenched with 1N sodium hydroxide (10 ml), extracted with methylene chloride (3×60 ml) and washed with brine (3×60 ml). The organic layer was dried over anhydrous sodium sulfate and filtered. Chromatography (10% methanol-ethyl acetate) afforded 0.52 g (22%) of product as a white foam; MS EI m/e 428 (M+).

INTERMEDIATE 5

5-Fluoro-3-{(1,4-trans)-4-[4-(3-methoxy-thiophen-2-yl)-3,6-dihydro-2H-pyridin-1-yl]-cyclohexyl}-1H-indole The trans compound was isolated at same time as the cis isomer in 2.5% yield (0.06 g) as a clear oil; MS EI m/e 428 (M+).

EXAMPLE 1

5-Fluoro-3-{(1,4-cis)-4-[4-(3-methoxy-thiophen-2-yl)-3,6-dihydro-2H-pyridin-1-yl]-cyclohexyl}-1H-indole A solution of (0.42 g) of Intermediate 4 in 20 ml acetic acid was heated at 70° C. for 0.5 hours. The reaction mixture was poured into 100 ml 2.5 N sodium hydroxide, and extracted with methylene chloride. The organic layer was dried over anhydrous sodium sulfate and filtered. Chromatogaphy (10% ethyl acetate-hexanes) afforded 0.32 g of product as a yellow oil, MS EI m/e 410 (M+).
The HCl salt was prepared in ethyl acetate: mp 64–167° C. Elemental analysis for $C_{24}H_{27}FOSN_2 \cdot HCl \cdot 1.25H_2O \cdot 0.07C_4H_8O_2$ Calc'd: C, 61.39; H, 6.55; N, 5.97 Found: C, 61.50; H, 6.19; N, 6.02

EXAMPLE 2

5-Fluoro-3-{(1,4-trans)-4-[4-(3-methoxy-thiophen-2-yl)-3,6-dihydro-2H-pyridin-1-yl]-cyclohexyl}-1H-indole This compound was prepared in the manner described above for Example 1 with the exception that Intermediate 5 (0.48 g) in 20 ml acetic acid was heated to provide in 70% (0.0.32 g) yield of product as a white solid: mp 190.5–191.5° C.
The HCl salt was prepared in ethyl acetate: mp 253.5–255.5° C.
Elemental analysis $C_{24}H_{27}FOSN_2 \cdot HCl$. Calc'd: C, 64.49; H, 6.31; N, 6.27 Found: C, 64.07; H, 6.22; N, 6.01
The activity of the present compounds is demonstrated by the following standard pharmacological test procedures.
The PCR cloning of the human 5-HT$_{1A}$ receptor subtype from a human genomic library has been described previously by Chanda et al., *Mol. Pharmacol.*, 43:516 (1993). A stable Chinese hamster ovary cell line expressing the human 5-HT$_{1A}$ receptor subtype (5-HT$_{1A}$.CHO cells) was employed throughout this study. Cells were maintained in DMEM supplemented with 10% fetal calf serum, non-essential amino acids and penicillin/ streptomycin.
Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and maintained at –80.C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 μL of buffer. Comparison experiments were performed by using 7 concentrations of unlabelled drug and a final ligand concentration of 1.5 nM. Non-specific binding was determined in the presence of 10 μM 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, Md.) through a GF/B filter presoaked for 30 minutes in 0.5% polyethyleneimine.

A protocol similar to that used by Cheetham et al., *Neuropharmacol.*, 32:737 (1993) was used to determine the affinity of compounds for the serotonin transporter. Briefly, frontal cortical membranes prepared from male Sprague-Dawley rats were incubated with $^3$H-paroxetine (0.1 nM) for 60 min at 25° C. All tubes also contained either vehicle, test compound (one to eight concentrations), or a saturating concentration of fluoxetine (10 μM) to define specific binding. All reactions were terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to Ki values using the method set forth in Cheng and Prusoff, *Biochem. Pharmacol.*, 22:3099 (1973) (Ki=IC50/((Radioligand conc.)/(1+KD)).

The [$^{35}$S]-GTPλS binding assay was similar to that used by Lazareno and Birdsall, *Br. J. Pharmacol.* 109:1120 (1993). Briefly, 5-HT$_{1A}$ cloned receptor membrane fragments (as used for 5-HT$_{1A}$ receptor binding assays) were stored at –70° C. When needed, membranes were rapidly thawed, centrifuged at 40,000× g for 10 minutes and resuspended at 4° C. for 10 minutes in assay buffer (25 mM HEPES, 3 mM MgCl$_2$, 100 mM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions were terminated by the addition of ice cold Tris buffer followed by rapid filtration using a Tom Tech® filtration device to separate bound from free [$^{35}$S]GTPgS. Agonists produced an increase in the amount of [$^{35}$S]GTPgS bound whereas antagonists produced no increase in binding. Bound radioactivity was counted and analyzed as above.

The following assays were performed by incubating the cells with DMEM containing 25 mM HEPES, 5 mM theophylline and 10 μM pargyline for a period of 20 minutes at 37° C. Functional activity was assessed by treating the cells with forskolin (1 uM final concentration) followed immediately by test compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at –20° C. prior to assessment of cAMP formation by a cAMP SPA assay (Amersham).

The compounds tested correspond to those prepared in Examples 1 and 2 above. The results of the procedures are set forth in Table 1.

| Example No. | 5-HT$_{1A}$ (Ki, nM) | ST (K$_i$, nM,) |
|---|---|---|
| 1 | 48% @ 1000 nM | 2.5 |
| 2 | 20.4 | 18% @ 100 nM |

As demonstrated by the results set forth above, the compounds of the present invention are active towards 5HT1A receptors and generally elevate serotonin levels by inhibiting 5-HT transport. Accordingly, the present compounds should be useful in treating disorders related to defects in serotonin concentration.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g., tablets or capsules. In such form, the compositions may be sub-divided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula:

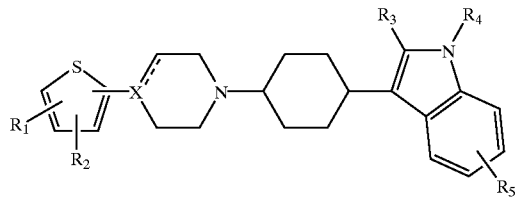

wherein:

X is carbon or nitrogen;

$R_1$ and $R_2$ are each, independently, hydrogen, halogen, $CF_3$, alkyl, alkoxy, or $MeSO_2$;

$R_3$ is hydrogen, halogen, or alkyl;

$R_4$ is hydrogen, alkyl, alkylaryl, or aryl; and $R_5$ is hydrogen, halogen, $CF_3$, CN, carbamide, or alkoxy; or pharmaceutically acceptable salts thereof.

2. A compound as in claim 1 wherein:

X is carbon;

$R_1$ and $R_2$ are each, independently, hydrogen or alkoxy;

$R_3$ is hydrogen;

$R_4$ is hydrogen; and $R_5$ is halogen; or pharmaceutically acceptable salts thereof.

3. The compound of claim 1 which is 5-Fluoro-3-{(1,4-cis)-4-[4-(3-methoxy-thiophen-2-yl)-3,6-dihydro-2H-pyridin-1-yl]-cyclohexyl}-1H-indole.

4. The compound of claim 1 which is 5-Fluoro-3-{(1,4-trans)-4-[4-(3-methoxy-thiophen-2-yl)-3,6-dihydro-2H-pyridin-1-yl]cyclohexyl}-1H-indole.

5. A pharmaceutical composition comprising a compound of the formula:

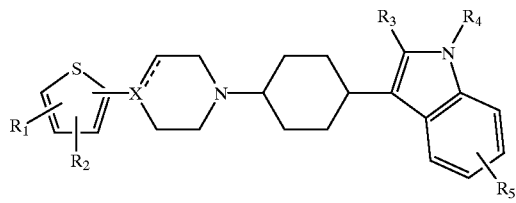

wherein:
- X is carbon or nitrogen;
- $R_1$ and $R_2$ are each, independently, hydrogen, halogen, $CF_3$, alkyl, alkoxy, or $MeSO_2$;
- $R_3$ is hydrogen, halogen, or alkyl;
- $R_4$ is hydrogen, alkyl, alkylaryl, or aryl; and
- $R_5$ is hydrogen, halogen, $CF_3$, CN, carbamide, or alkoxy; or pharmaceutically acceptable salts thereof.

6. A method of treating depression in a patient in need thereof comprising administering to said patient an antidepressant effective amount of a compound of the formula:

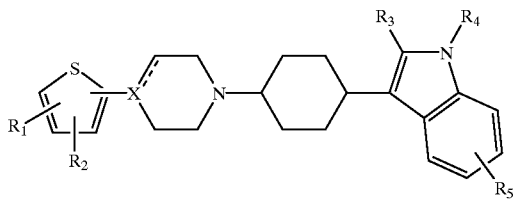

wherein:
- X is carbon or nitrogen;
- $R_1$ and $R_2$ are each, independently, hydrogen, halogen, $CF_3$, alkyl, alkoxy, or $MeSO_2$;
- $R_3$ is hydrogen, halogen, or alkyl;
- $R_4$ is hydrogen, alkyl, alkylaryl, or aryl; and
- $R_5$ is hydrogen, halogen, $CF_3$, CN, carbamide, or alkoxy; or pharmaceutically acceptable salts thereof.

\* \* \* \* \*